US009855397B2

(12) United States Patent
Peake et al.

(10) Patent No.: US 9,855,397 B2
(45) Date of Patent: Jan. 2, 2018

(54) SOUND DAMPENING IN POSITIVE AIRWAY PRESSURE DEVICES

(75) Inventors: Gregory Robert Peake, Kingsford (AU); Jeffrey Peter Armitstead, North Sydney (AU); Paul Andrew Dickens, Springwood (AU); Dmitri Anatolievich Doudkine, Chatswood (AU); Robert Edward Henry, Baulkham Hills (AU); Liam Holley, Marrickville (AU); Gerard Michael Rummery, Woodford (AU); Lee James Veliss, Freshwater (AU)

(73) Assignee: ResMed Limited, Bella Vista (AU)

( * ) Notice: Subject to any disclaimer, the term of this patent is extended or adjusted under 35 U.S.C. 154(b) by 1557 days.

(21) Appl. No.: 13/389,498

(22) PCT Filed: Aug. 4, 2010

(86) PCT No.: PCT/AU2010/000983
§ 371 (c)(1),
(2), (4) Date: Feb. 8, 2012

(87) PCT Pub. No.: WO2011/017738
PCT Pub. Date: Feb. 17, 2011

(65) Prior Publication Data
US 2012/0145155 A1 Jun. 14, 2012

Related U.S. Application Data

(60) Provisional application No. 61/272,044, filed on Aug. 11, 2009.

(51) Int. Cl.
*A61M 16/00* (2006.01)
*A61M 16/08* (2006.01)
*A61M 16/10* (2006.01)

(52) U.S. Cl.
CPC .... *A61M 16/0875* (2013.01); *A61M 16/0816* (2013.01); *A61M 16/0066* (2013.01);
(Continued)

(58) Field of Classification Search
CPC .......... A61M 16/0875; A61M 16/0816; A61M 16/0066; A61M 2205/42
(Continued)

(56) References Cited

U.S. PATENT DOCUMENTS 3,476,210 A * 11/1969 Carlson ................... H04L 13/02
178/42
3,545,566 A * 12/1970 Abrahamsson ........... F01N 1/10
128/200.14
(Continued)

FOREIGN PATENT DOCUMENTS

KR 2004059520 A * 7/2004
WO WO 1999/022793 5/1999

OTHER PUBLICATIONS

International Search Report for PCT/AU2010/000983, dated Oct. 11, 2010.

*Primary Examiner* — (Jackie) Tan-Uyen T Ho
*Assistant Examiner* — Jonathan Paciorek
(74) *Attorney, Agent, or Firm* — Nixon & Vanderhye P.C.

(57) ABSTRACT

A CPAP system includes a PAP device (5) structured to generate a supply of pressurized air, a patient interface (15) adapted to engage with the patient's face to provide a seal, an air delivery conduit (102,104) provided between the PAP device and the patient interface to deliver the supply of pressurized air along a gas delivery path from the PAP device to the patient interface, and a muffler (100) provided along the gas delivery path downstream of the PAP device.

23 Claims, 18 Drawing Sheets

(52) U.S. Cl.
CPC ....... *A61M 16/106* (2014.02); *A61M 16/1055* (2013.01); *A61M 2205/42* (2013.01)

(58) Field of Classification Search
USPC ............ 128/205.12, 204.18, 200.13, 200.24, 128/203.14, 203.24, 204.21, 204.22, 128/204.23, 206.15
See application file for complete search history.

(56) References Cited

U.S. PATENT DOCUMENTS

| | | | |
|---|---|---|---|
| 3,995,712 A * | 12/1976 | Leistritz et al. .............. | 181/230 |
| 5,809,996 A * | 9/1998 | Alldredge ......... | A61M 15/0086 |
| | | | 128/200.14 |
| 6,595,319 B1 * | 7/2003 | Huff .......................... | F01N 1/02 |
| | | | 181/250 |
| 6,615,831 B1 | 9/2003 | Tuitt et al. | |
| 7,328,586 B2 * | 2/2008 | Gau et al. ....................... | 62/158 |
| 7,448,382 B1 | 11/2008 | Alexander et al. | |
| 2003/0172931 A1 * | 9/2003 | Kerechanin et al. .... | 128/204.18 |
| 2004/0226562 A1 | 11/2004 | Bordewick | |
| 2005/0150801 A1 * | 7/2005 | Tippey .................... | B65D 5/68 |
| | | | 206/440 |
| 2006/0144396 A1 * | 7/2006 | DeVries et al. ......... | 128/204.21 |
| 2007/0169781 A1 * | 7/2007 | Tang .................... | A61M 16/00 |
| | | | 128/206.21 |
| 2008/0072900 A1 | 3/2008 | Kenyon et al. | |
| 2008/0127976 A1 * | 6/2008 | Acker .................. | A61M 16/08 |
| | | | 128/204.18 |
| 2008/0257346 A1 | 10/2008 | Lathrop et al. | |
| 2012/0121441 A1 * | 5/2012 | Morrison ........................ | 417/53 |

\* cited by examiner

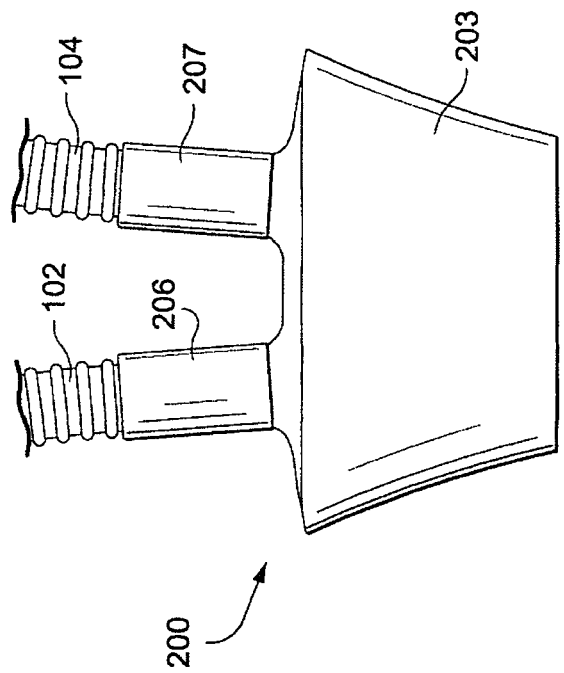
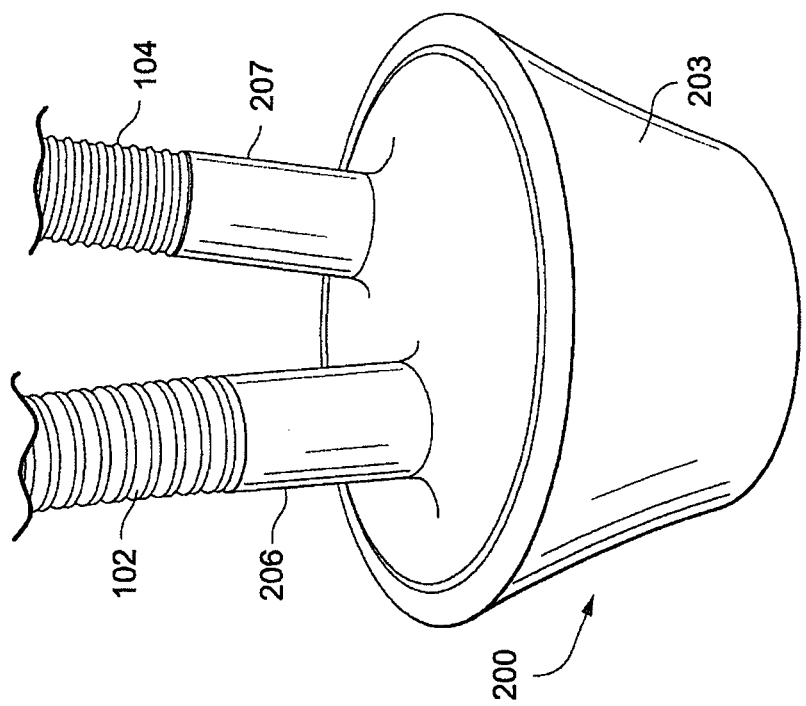

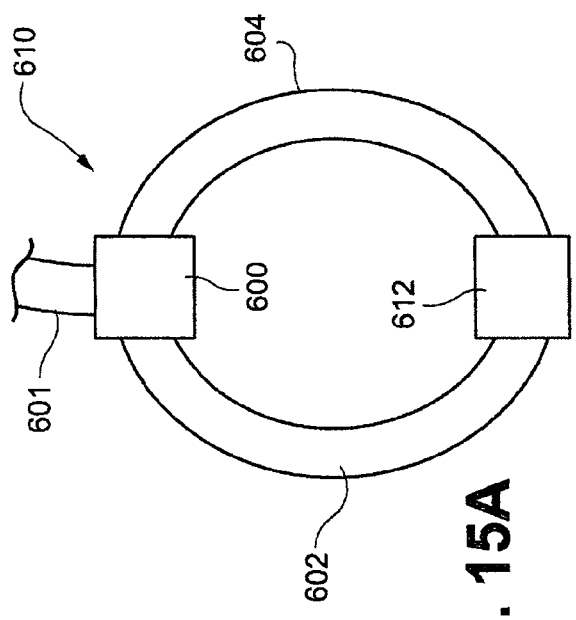
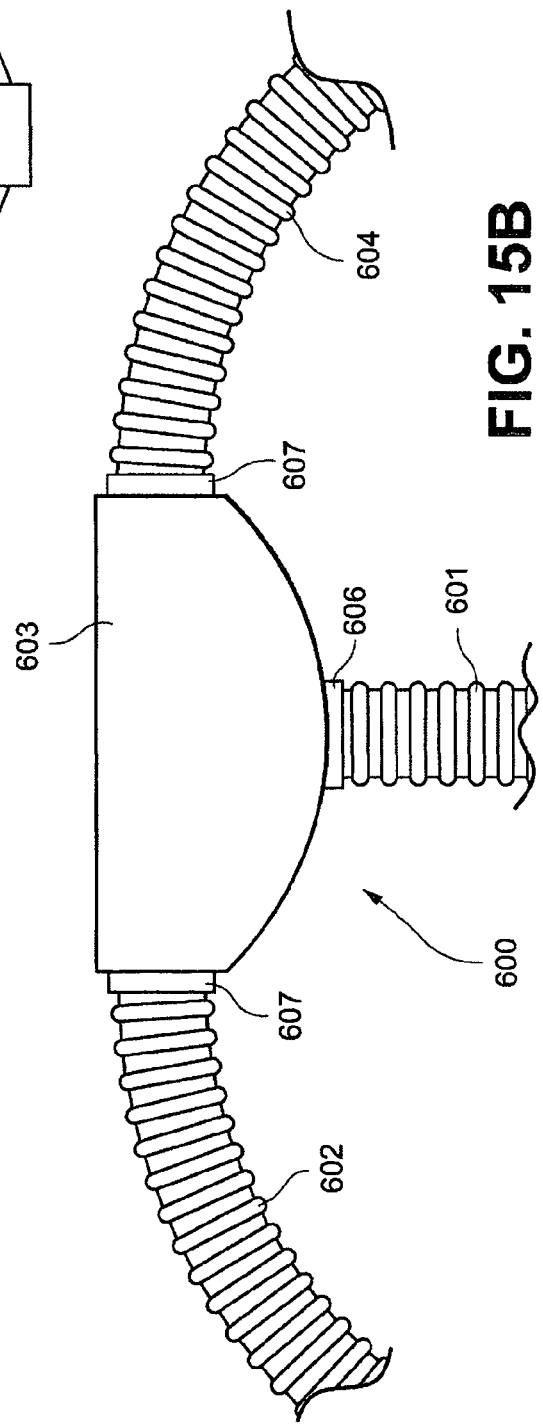
FIG. 15A
FIG. 15B

SOUND DAMPENING IN POSITIVE AIRWAY PRESSURE DEVICES

CROSS-REFERENCE TO APPLICATIONS

This application is the U.S. national phase of International Application No. PCT/AU2010/000983, filed Aug. 4, 2010, which designated the U.S. and claims the benefit of U.S. Provisional Patent Application No. 61/272,044, filed Aug. 11, 2009, each of which are incorporated herein by reference in its entirety.

FIELD OF THE INVENTION

The field of the invention generally relates to positive airway pressure devices and masks used therewith. More specifically, the field of the invention relates to sound dampening in the flow passageways of positive airway pressure devices and the masks used therewith.

BACKGROUND OF THE INVENTION

Sleep apnea is a sleep disorder commonly characterized by pauses in breathing during sleep. These episodes, called apneas, each last long enough so one or more breaths are missed, and occur repeatedly throughout sleep. The standard definition of any apneic event includes a minimum ten second interval between breaths, with either a neurological arousal (three-second or greater shift in EEG frequency, measured at C3, C4, O1, or O2), or a blood oxygen desaturation of three-four percent or greater, or both arousal and desaturation. Sleep apnea is diagnosed with an overnight sleep test called a polysomnogram.

Often, the individual with sleep apnea is unaware of having difficulty breathing, even upon awakening. Sleep apnea is recognized as a problem by others witnessing the individual during episodes or is suspected because of its effects on the body. Symptoms may be present for years, even decades without identification, during which time the sufferer may become conditioned to the daytime sleepiness and fatigue associated with significant levels of sleep disturbance.

Fortunately, sleep apnea is treatable. Some treatments involve lifestyle changes, such as avoiding alcohol and medications that relax the central nervous system (for example, sedatives and muscle relaxants), losing weight, and quitting smoking. Some people are helped by special pillows or devices that keep them from sleeping on their backs, or oral appliances to keep the airway open during sleep. If these methods are inadequate, doctors often recommend continuous positive airway pressure (CPAP) therapy, in which a face mask is attached to a tube and a machine that blows pressurized air into the mask and through the airway to keep it open. (See Wikipedia: Sleep Apena, available at—http://en.wikipedia.org/wiki/Sleep_apnea).

Since sleep apnea occurs when a person is sleeping, devices and therapies used to treat sleep apnea should generally be designed so as not to significantly interfere with a person's sleep.

Devices that prevent a person from rolling over may interfere with sleep to a lesser extent, insomuch as they prevent a person from sleeping in a certain position. CPAP devices, on the other hand, while moderately quiet, do blow a continuous stream of forced air into a patient's mouth/nose. Further, the patient also exhales, and there is cyclic noise from the patient's natural breathing. While people may not typically snore or breathe loudly enough to wake themselves up, CPAP devices have tubing included therein which can resonate and amplify sound, and some of the tubing may even run near a patient's ear or ears, thus delivering the sound directly past the source of hearing. CPAP devices may also generate noise from operation of the motor of the flow generator, the sound of the air moving through the tubing and/or mask, and the noise of air leaving various vents in the mask or tubing. All of these factors (e.g., conducted noise as well as radiated noise) can contribute to noise in the CPAP system that may adversely affect patient and/or bed partner comfort, depending on both the magnitude and character of the noise. Moreover, excessive noise can lead to patients being non-compliant with CPAP therapy.

There is a long felt and continuing need to reduce the noise associated with CPAP therapy. Reducing the noise associated with CPAP therapy can significantly improve the user friendliness and compliance of CPAP treatment.

SUMMARY OF THE INVENTION

One aspect of the invention relates to a muffler system for CPAP systems. Installable at a variety of locations and constructed in a variety of forms, the mufflers can help reduce noise in the CPAP system and help prevent system noise from adversely affecting the patient and/or bed partner. The mufflers may be constructed in a collapsible form, so that they are easier or more portable to travel with.

In an embodiment, exemplary forms for mufflers include, but are not limited to, a bottle-shaped form, an "artistic" sculptural form, a biscuit-shaped form, and a half-biscuit form. Numerous other suitable shapes would also be possible.

In an embodiment, the mufflers may be adapted to adhere to surfaces using, for example, suction cups or hook-and-loop fasteners or to hang from a bedpost or hook by forming a loop of the tubing. The mufflers may also be provided with one or more clear surfaces, both to display internal technology and to add to the visual appeal of the device.

In an embodiment, internal workings of the muffler may have various configurations, including, but not limited to, a simple hollow chamber, a chamber with one or more baffles, a chamber with filters, a chamber with a perforated internal pipe, a chamber with a flexible membrane, a chamber with a microperforated panel, or some combination of the preceding. The chamber size may also be adjustable through various adjustment capabilities provided to the muffler.

In an embodiment, a plurality of mufflers may also be included in a muffling system. For example, a first muffler can be included at some point along the tubing to muffle the noise of the PAP device (i.e., the device which blows air to the patient). Since noise is generated both by air as it passes out of the tubing and by the motor of the device, allowing the expansion to occur (at least once) before the air reaches the patient, along with a chamber designed to muffle at least some of the motor noise traveling along the tubing, helps muffle the PAP noise. In addition, a smaller muffler may be provided in the vicinity of the patient interface, so as to reduce cyclic noise, including the noise generated by the patient's breathing.

Another aspect of the invention relates to a CPAP system including a PAP device structured to generate a supply of pressurized air, a patient interface adapted to engage with the patient's face to provide a seal, an air delivery conduit provided between the PAP device and the patient interface to deliver the supply of pressurized air along a gas delivery path from the PAP device to the patient interface, and a muffler provided along the gas delivery path downstream of the PAP device.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 11A is a perspective view of a sculpture-shaped muffler according to an embodiment of the present invention;

FIG. 11B is a side view of the sculpture-shaped muffler shown in FIG. 11A showing its flat base;

FIG. 15A is a schematic view showing a muffler included in a patient interface according to an embodiment of the present invention;

FIG. 15B is an enlarged view showing the muffle of FIG. 15A; and

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

1. Continuous Positive Airway Pressure (CPAP) System

A CPAP system generally includes a Positive Airway Pressure (PAP) device or flow generator, an air delivery conduit or tubing, and a patient interface. In use, the PAP device generates a supply of pressurized air that is delivered to the patient via an air delivery conduit that includes one end coupled to the outlet of the PAP device and an opposite end coupled to the patient interface. The patient interface comfortably engages the patient's face and provides a seal. The patient interface may have any suitable configuration as is known in the art, e.g., full-face mask, nasal mask, oro-nasal mask, mouth mask, nasal prongs, etc. All of the embodiments may also be used with other respiratory assist or support devices and/or suitable medical devices, e.g., medical device including an airpath where noise is a potential problem for patients.

2. Mufflers

The following provides mufflers according to embodiments of the present invention. Each muffler may be provided downstream of the PAP device. For example, each muffler may be positioned along the length of the air delivery conduit, upstream of the patient interface, and at the inlet to the patient interface. Each muffler may be structured to dampen, muffle, and/or reduce noise generated by the CPAP system in use.

In embodiments (e.g., see FIGS. 1 and 5 described below), the muffler may be positioned downstream from the flow of air generated by the PAP device. As illustrated, each muffler may be connected by a relatively short length of tubing from the PAP device and a relatively longer length of tubing to the patient interface, e.g., mask.

Figure 1:
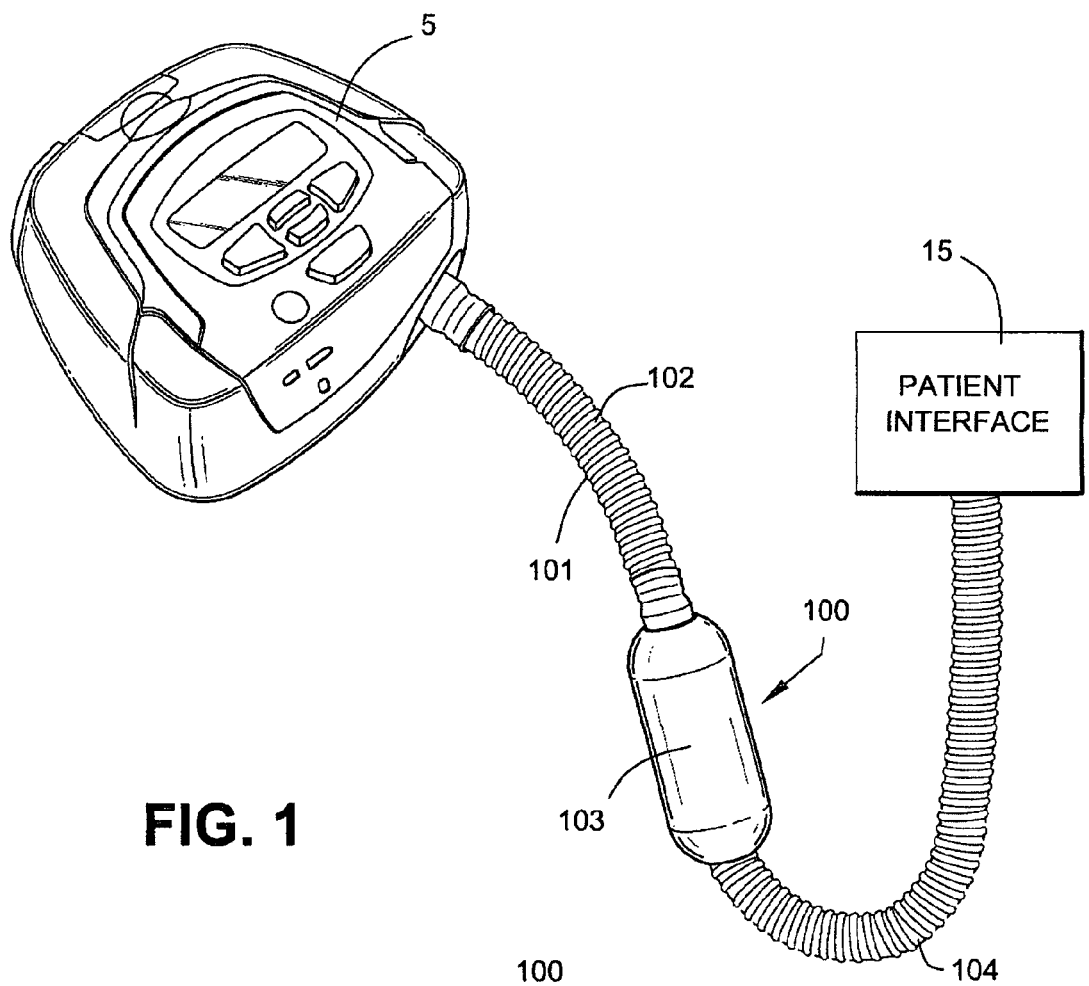
FIG. 1 shows a CPAP system including a bottle-shaped muffler according to an embodiment of the present invention.
Figure 5:
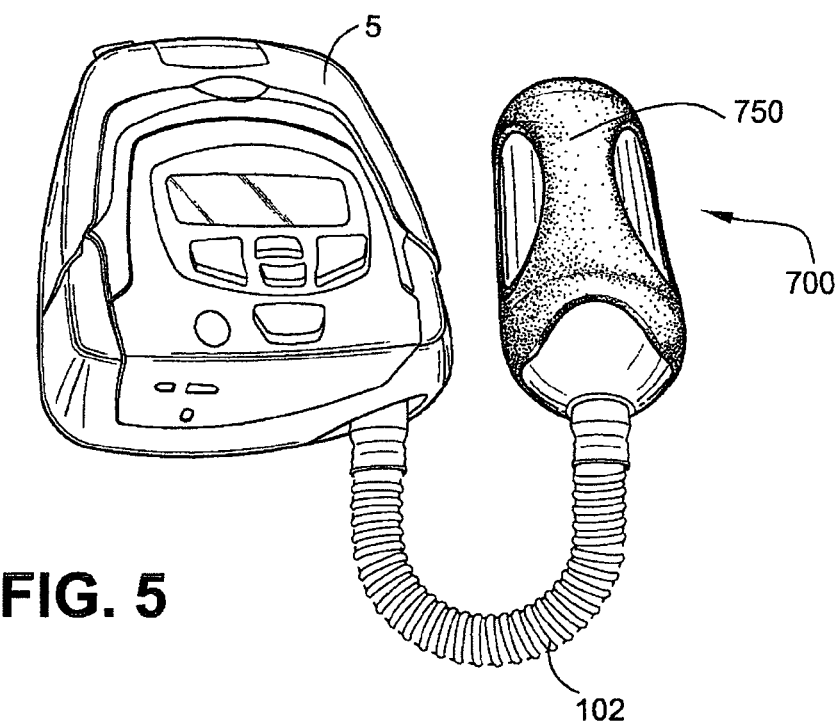
FIG. 5 shows a CPAP system including a bottle-shaped muffler according to another embodiment of the present invention.
Figure 6:
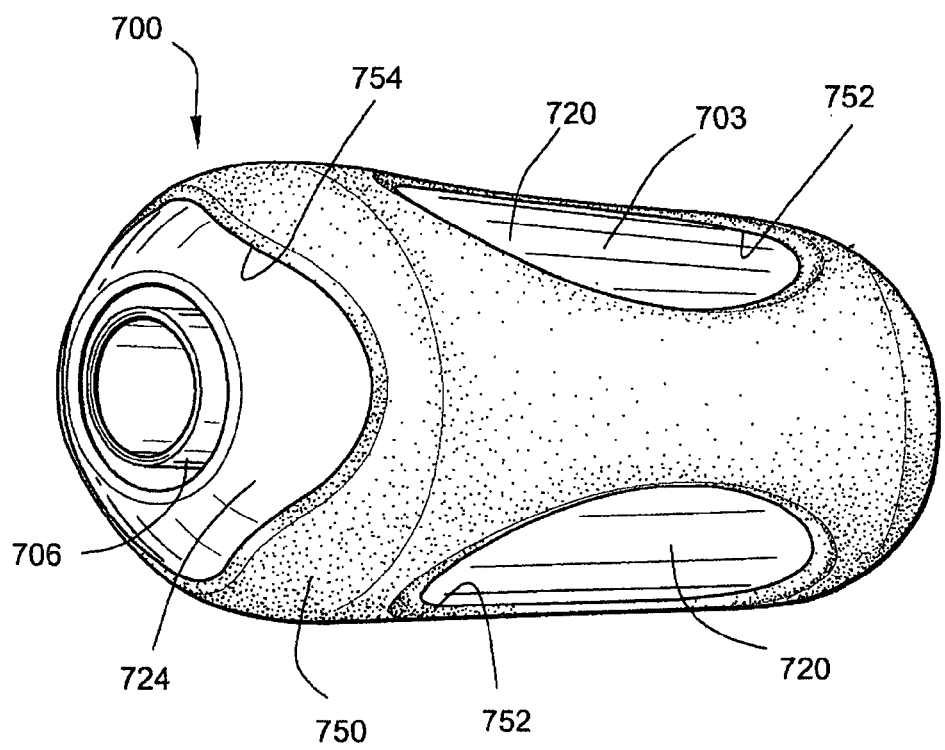
FIG. 6 is a perspective view of the bottle-shaped muffler of FIG. 5.
Figure 7:
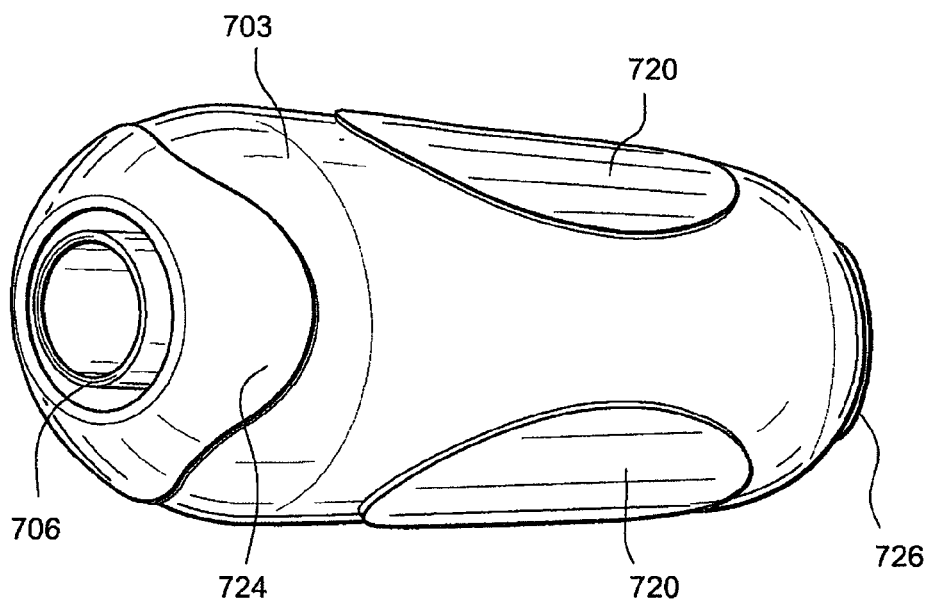
FIG. 7 is a perspective view of the bottle-shaped muffler of FIG. 5 with the casing removed.
Figure 8:
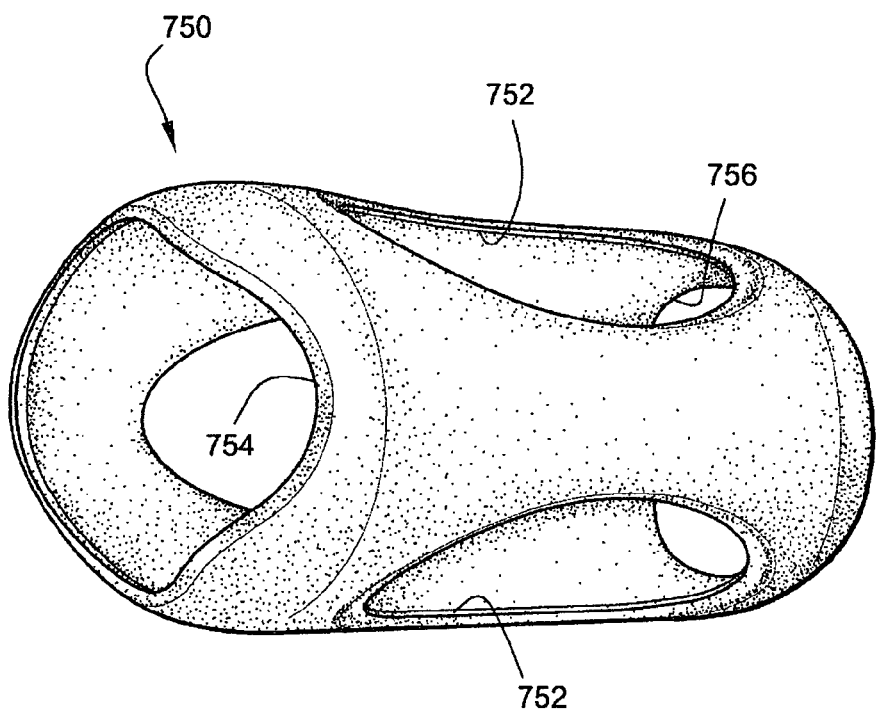
FIG. 8 is a perspective view of a casing of the bottle-shaped muffler of FIG. 5.

The muffler in FIGS. 1 and 5 may be positioned by differing lengths of tubing so that the muffler may be positioned closer to the PAP device than the patient interface. This arrangement may reduce the weight and/or bulk carried or supported by the patient interface, which may optimize mask fit.

In FIGS. 1 and 5 the muffler is separated by a small distance from the PAP device. This arrangement may allow for different PAP devices to be used so long as the tubing can be adapted to fit the connection points.

Also, the muffler may be constructed to be a disposable item, e.g., constructed from relatively cheap construction materials (e.g., plastic) to infer disposability. Disposability may reduce the requirements for cleaning the muffler by the patient.

In an embodiment, the muffler may be constructed as large as possible to increase the overall muffling effect. However, the size of the muffler may be balanced with the consideration to make the muffler relatively light and portable for the patient and not overly bulky, e.g., for travel. Also, the chamber of the muffler may be variable in size so that the muffler may be tuned to specific muffling requirements. For example, a single muffler may be used having a variable chamber size for use with various blowers/CPAP systems, i.e., no need to change muffler size for each CPAP system.

2.1 Bottle-shaped Muffler

FIGS. 1-4 illustrate a bottle-shaped or pipe-type muffler 100 according to an embodiment of the present invention. The muffler 100 is structured to be coupled between the PAP device 5 and the patient interface 15, e.g., the muffler 100 may be installed anywhere along the length of tubing leading from the PAP device to the patient interface. By providing a muffler 100 along the tubing, the amount of noise conducted to the patient interface may be greatly reduced.

The muffler 100 includes a main body 103, a first connecting portion 106 (e.g., an inlet portion or port), and a second connecting portion 107 (e.g., an outlet portion or port). The general bottle shape arrangement of the muffler is generated by the generally hollow tubular shape with rounded ends (e.g., see FIG. 4). The connection portions 106, 107 are provided in the center of respective rounded ends. The muffler 100 provides an inline arrangement in which the main body 103 and connecting portions 106, 107 are aligned along the axis of the muffler. A first air delivery conduit 102 (inlet piece of tubing) is coupled between the PAP device 5 and the first connecting portion 106 and a second air delivery conduit 104 (outlet piece of tubing) is coupled between the patient interface 15 and the second connecting portion 107. The conduits 102, 104 may be pushed onto respective connection portions 106, 107 by the user, and the conduits may be adapted to constrict around the connection point and generate a seal.

Figure 2:
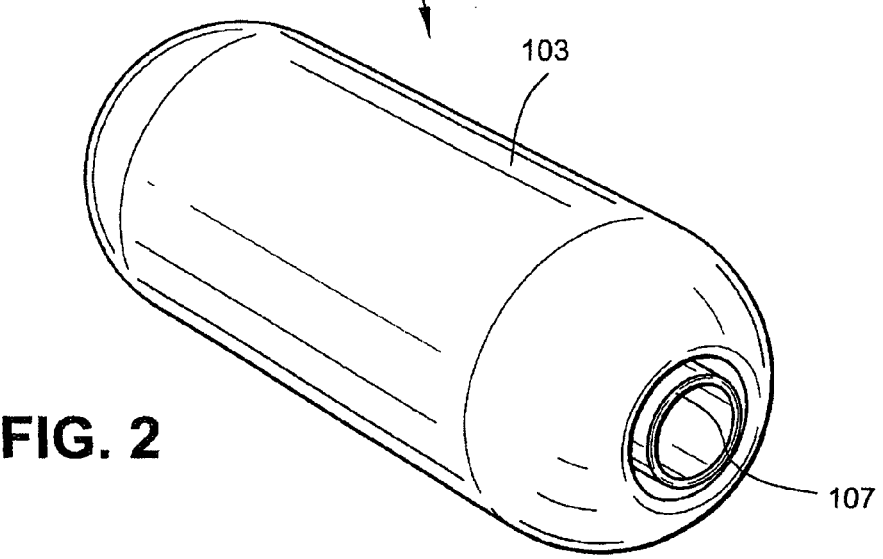
FIG. 2 is a perspective view of the bottle-shaped muffler of FIG. 1.
Figure 3:
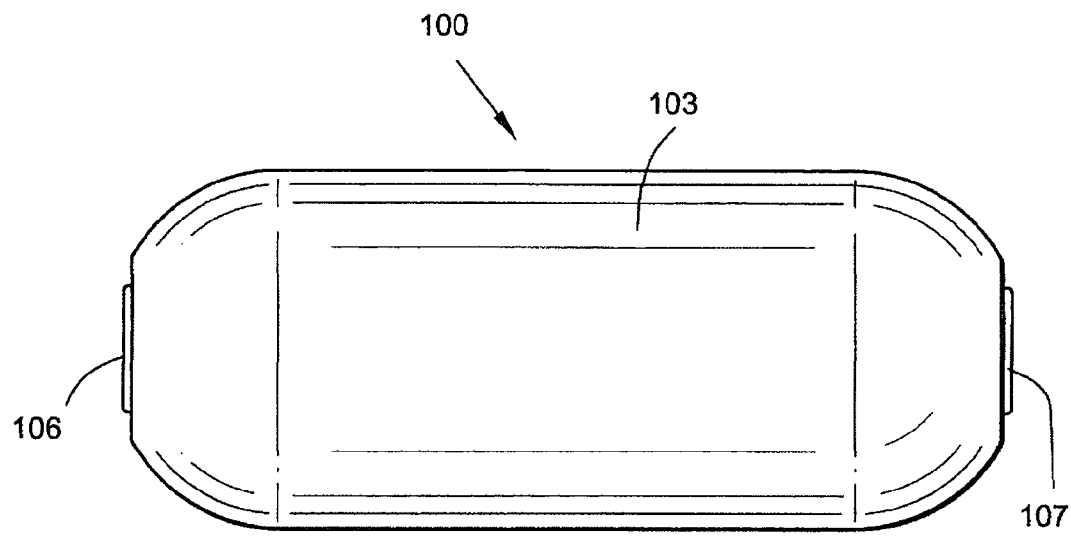
FIG. 3 is a side view of the bottle-shaped muffler of FIG. 1.
Figure 4:
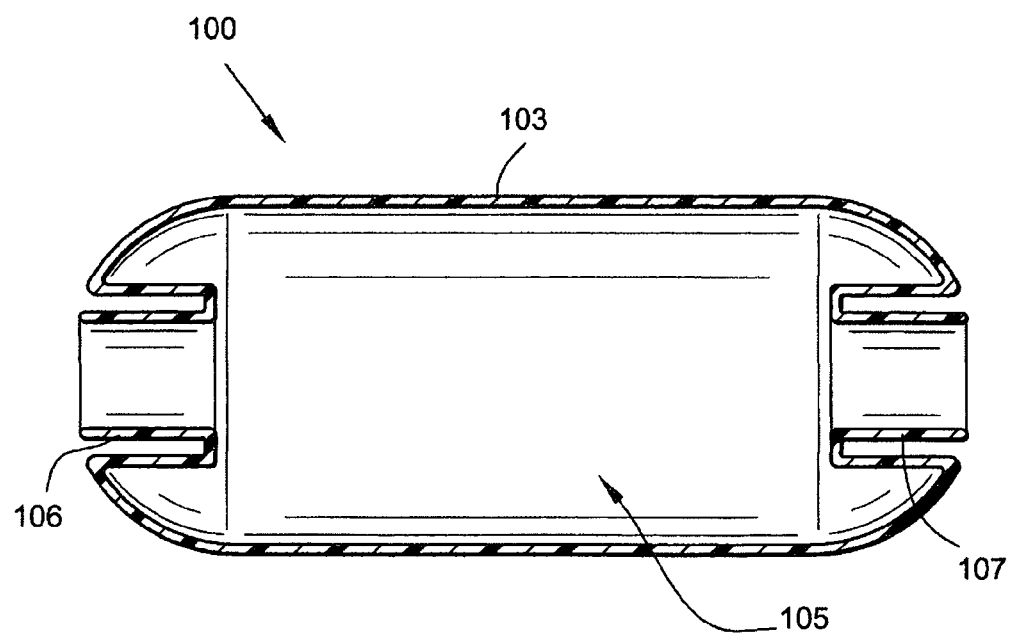
FIG. 4 is a cross-sectional view of the bottle-shaped muffler of FIG. 1.
Figure 10:
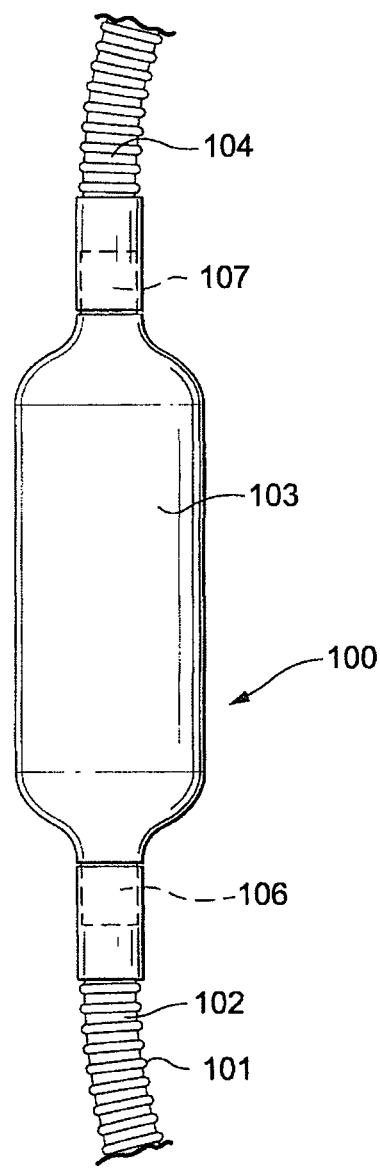
FIG. 10 shows a bottle-shaped muffler according to another embodiment of the present invention.

As best shown in FIGS. 2 and 4, the first and second connecting portions 106, 107 are in the form of recessed ports or tubes, which extend into the expansion chamber 105 provided by the main body 103. Such arrangement provides a sudden change in cross-sectional area for gas entering and exiting the chamber (e.g., relatively small diameter tube of connection portion entering into larger volume of the chamber), which may be at least partially determinative in enhancing muffling performance. In an alternative embodiment, as shown in FIG. 10, the first and second connecting portions 106, 107 may protrude outwardly from respective ends of the main body 103 so as to provide a smooth or gradual entry/exit channel into the chamber.

In an embodiment, the orientation of the muffler may not be relevant, i.e., the first air delivery conduit 102 may be coupled to either connecting portion 106, 107 of the muffler. That is, the muffler may be connected along the air flow path of the PAP device in either direction as both sides of the muffler are symmetrical. This arrangement may facilitate usability by reducing the overall difficulty of installing the muffler along the air flow path.

In use, the first connecting portion 106 is adapted to receive a supply of pressurized gas, which passes through the main body 103 and then exits the muffler via the second connecting portion 107. The main body 103 of the muffler 100 provides a volume or expansion chamber 105 structured to reduce or cancel out at least a portion of the noise produced by the sound waves traveling down the air tubing. That is, the muffler muffles conducted noise traveling to the patient interface. In addition, the muffler may also reduce radiated noise from the PAP device in use.

In addition to the muffler itself, the tubing can be provided with ribbing 101 to help reduce noise in the system. The ribbing may help deflect and disrupt sound waves and prevent them from traveling smoothly along the tubing.

The muffler can be positioned at various locations along the tubing and still produce the desired effect of reducing noise, although certain locations may have a better effect on noise or may be desirable for other reasons. For example, if the muffler were designed to be set down or attached to a flat surface, placing the muffler too close to the patient's head might defeat some of these intended purposes.

The muffler's volume or expanded chamber 105 absorbs and/or reflects (e.g., creating destructive interference) at least a portion of the sound waves traveling into the chamber. This prevents the full sound headed into the chamber from traveling out of the chamber and towards the patient.

In an embodiment, the muffler may be equipped with baffles, or deflecting walls structured to redirect and/or absorb sound-waves. The deflected sound waves may create destructive interference by overlapping with new sound waves to further muffle sound. In destructive interference, sound waves act to cancel each other out and reduce the overall system noise as perceived by the patient. In embodiments, the muffler will operate at least partially using destructive interference within the tubular body of the muffler to reduce the overall transmitted noise.

In an embodiment, the muffler may have a length of about 125-195 mm, e.g., 150 mm or 180 mm, and a diameter of about 50-80 mm, e.g., 60 mm or 65 mm. In an embodiment, the muffler includes a volume of about 300 cm$^3$. However, other suitable sizes are possible, e.g., depending on application, sound requirements, etc. In an embodiment, lengths less than about 40 cm may be more practical and suitable for patient use and comfort.

In an embodiment, the muffler may be constructed of a plastic material (e.g., molded in one-piece, molded of two or more pieces and then assembled to one another, etc.) or textile material (e.g., collapsible, inflatable, etc.). Exemplary materials include but are not limited to polypropylene or polyethylene. In an embodiment, one or more portions of the muffler may be constructed of a transparent material to allow users to visually check the cleanliness of the muffler, which is generally beneficial for use with medical applications. Also, the muffler 100 may include a high gloss surface finish and/or a casing, e.g., for aesthetics.

For example, FIGS. 5-9 illustrate a muffler 700 with a soft-touch outer casing or sleeve 750, e.g., to facilitate handling and enhance aesthetics. In an embodiment, the casing 750 may be constructed of silicone, thermoplastic elastomer, rubber, other relatively flexible elastic materials, or any other soft material that may be slid over the main body 703. As illustrated, such casing 750 includes a tubular construction that can at least partially enclose the tubular main body 703 of the muffler. The main body 703 is provided with recessed ports 706, 707 which extend into an expansion chamber as described above. FIG. 5 shows the muffler 700 coupled to the PAP device 5 by air delivery conduit 102.

In the illustrated embodiment, the casing includes one or more openings or cut outs to receive complimentary shaped protrusions on the main body, e.g., to axially retain the casing on the main body. For example, the casing 750 includes elongated, oval shaped openings 752 (e.g., three openings spaced around its perimeter) that receive complimentary, oval shaped protrusions 720 spaced around the perimeter of the main body 703. In addition, the openings 754, 756 at respective ends of the casing 750 are contoured along its perimeter so as to engage against complimentary shaped protrusions 724, 726 along respective ends of the main body 703.

The casing 750 may be formed separately from the main body 703 and attached thereto, or the casing 750 may be overmolded to the main body 703.

Figure 9:
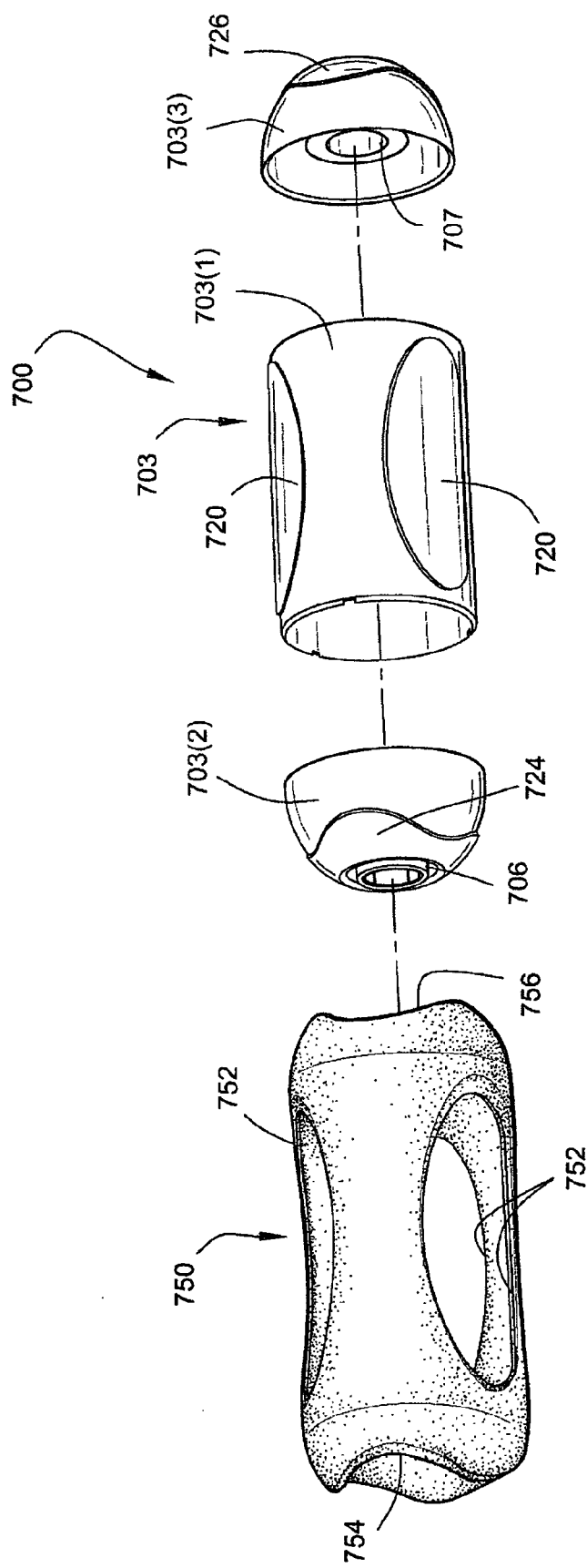
FIG. 9 is an exploded view of the bottle-shaped muffler of FIG. 5.

As shown in FIG. 9, the main body 703 may include three parts, i.e., a central portion 703(1) and rounded end portions 703(2), 703(3) (providing respective recessed ports 706, 707) that are formed (e.g., molded) separately from one another and then assembled to one another, e.g., allows disassembly for cleaning. For example, the end portions 703(2), 703(3) may be coupled to respective ends of the central portion 703(1) with a snap-fit, other suitable mechanical interlock, or permanently joined by welding or glue. Alternatively, the main body may be integrally formed in one piece, e.g., see main body 103 of FIGS. 1-4. In an embodiment, ends of the casing 750 may overhang the end portions 703(2), 703(3) and engage the end portions to pull them towards the main body and hold the end portions in position.

Additionally, the casing 750 may be constructed of a relatively slip resistant material to prevent the muffler from shaking or vibrating when placed on a hard surface or to prevent or limit additional noise. Furthermore, one or more projections may be provided on the outer surface of the casing 750 to prevent the muffler from accidentally rolling.

2.2 Sculpture-shaped Muffler

FIGS. 11A and 11B illustrate a sculpture-shaped muffler 200 according to an embodiment of the present invention. As illustrated, the muffler 200 includes a main body or base 203, a first connecting portion 206 adapted to connect to inlet tubing 102, and a second connecting portion 207 adapted to connect to outlet tubing 104. As shown in FIG. 11B, the base 203 of the muffler 200 includes a flat bottom surface, which allows the muffler to rest on a flat surface. In an embodiment, the base 203 may be weighted to maintain its position in use. Alternatively, the base 203 of the muffler can be provided with a suction cup or hook-and-loop fastener system, which may allow the muffler to be affixed to an appropriate surface. In an embodiment, the muffler 200 may provide a stable connection point for the tube to the patient interface, and may allow the PAP device to be hidden out of site. For example, a longer tube may be used to connect the PAP device to the muffler so that the muffler may be positioned on the patient's bedside table with the PAP device positioned out of site (e.g., in a drawer, under the bed, etc.). This arrangement not only improves conducted noise performance (via the muffler), but also provides a nicer visible aesthetic compared to the PAP device.

Similar to the above, the main body 203 of the muffler 200 provides a volume or chamber structured to reduce or cancel out at least a portion of the noise produced by the CPAP system in use.

For purposes of this specification, sculpture-shaped may include the shape and appearance of the muffler as depicted in FIGS. 11A and 11B.

2.3 Biscuit-shaped Muffler

Figure 12A:
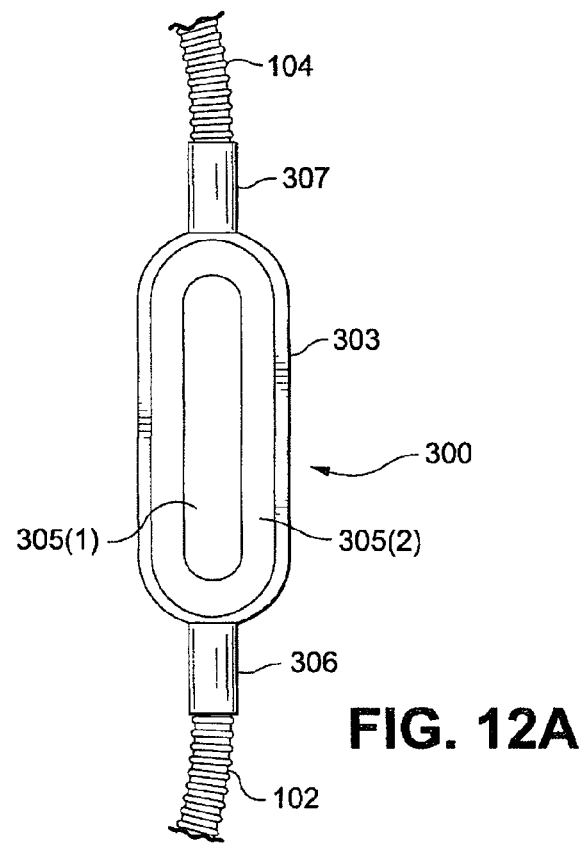
FIG. 12A is a top view of a biscuit-shaped muffler according to an embodiment of the present invention.
Figure 12B:
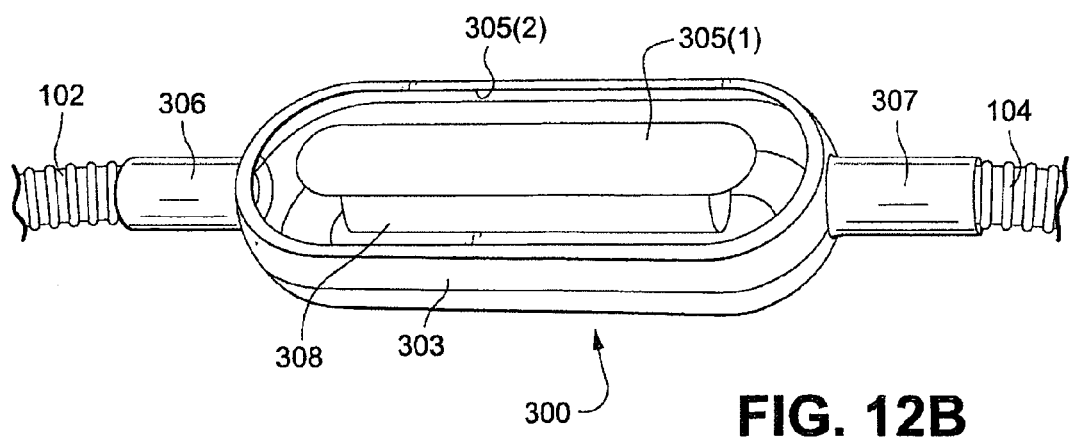
FIG. 12B is a perspective view of the biscuit-shaped muffler shown in FIG. 12A showing its baffle and clear viewing pane.

FIGS. 12A and 12B illustrate a biscuit-shaped muffler 300 according to an embodiment of the present invention. As illustrated, the muffler 300 has an oblong shape including a main body 303, a first connecting portion 306 adapted to connect to inlet tubing 102, and a second connecting portion 307 adapted to connect to outlet tubing 104. The upper wall of the muffler 300 is provided with a central opaque portion 305(1) and a clear portion 305(2) ringing or surrounding the opaque portion 305(1). The clear portion 305(2) allows the user to see the inner workings of the muffler 300 and also serves to provide an aesthetic touch to the muffler.

FIG. 12B illustrates the internal workings of the main body 303. As illustrated, the muffler 300 includes a filter 308 (e.g., anti-bacterial filter) underlying the opaque portion 305(1) and visible through the clear portion 305(2). In an embodiment, the main body may also include a baffle structured to absorb and divert sound waves, helping to create destructive interference to disrupt noise.

Similar to the above, the main body 303 of the muffler 300 provides a volume or chamber structured to reduce or cancel out at least a portion of the noise produced by the CPAP system in use. In addition, the main body 303 provides a filter 308 to filter the air passing therethrough.

Figure 13:
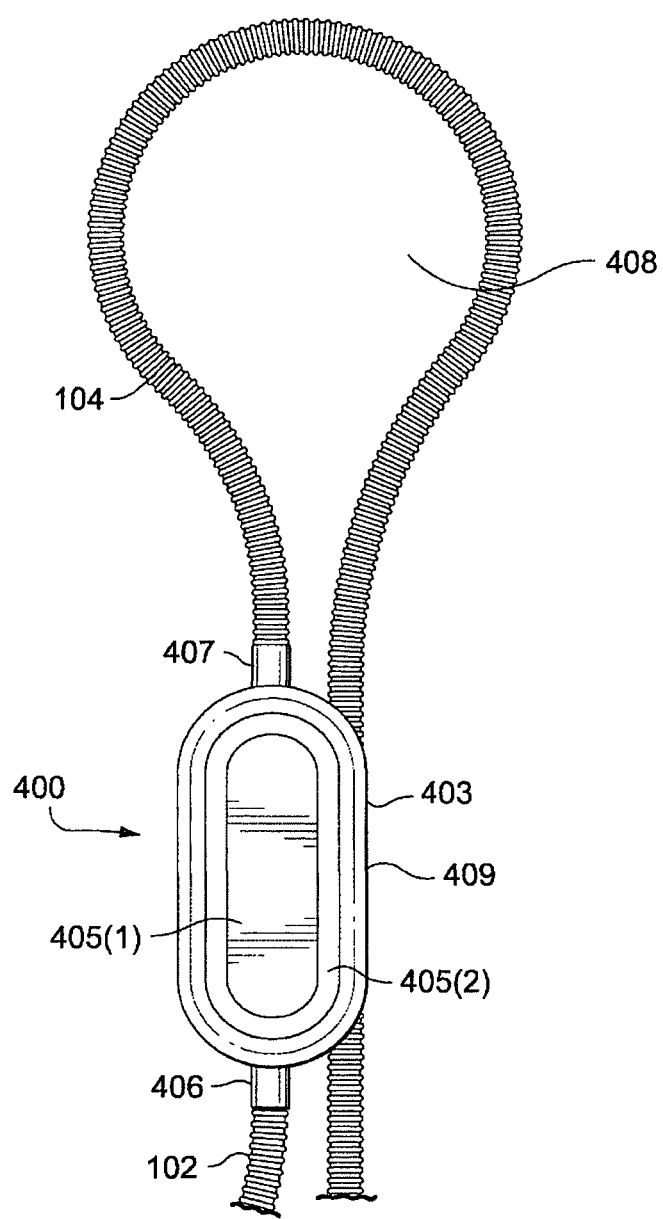
FIG. 13 shows a biscuit-shaped muffler including integrated tube management according to an embodiment of the present invention.

FIG. 13 illustrates a biscuit-shaped muffler 400 including integrated tube management according to an embodiment of the present invention. As illustrated, the muffler 400 includes a main body 403, a first connecting portion 406 adapted to connect to inlet tubing 102, and a second connecting portion 407 adapted to connect to outlet tubing 104. Also, the upper wall of the muffler 400 includes inner portion 405(1) and outer portion 405(2) (e.g., which may be clear and/or opaque), e.g., to provide visual lightness. It should be appreciated that the portions 405(1), 405(2) may be all clear, all opaque, translucent, or some combination of the preceding.

In addition, the muffler 400 includes an in-line tube connection or management portion 409. In the illustrated embodiment, the connection portion 409 includes a groove provided to the side of the muffler into which the tube 104 can be removably attached. Additional connective pieces, such as rings, clasps, etc., might also be used to removably attach the tube to the muffler.

Once the tube is attached, the tubing 104 may form a loop 408. The loop 408 can be hooked around a bed post or other suitable object in order to keep the tubing in a desired position/location and reduce tube drag.

2.4 Half-biscuit-shaped Muffler

Figure 14B:
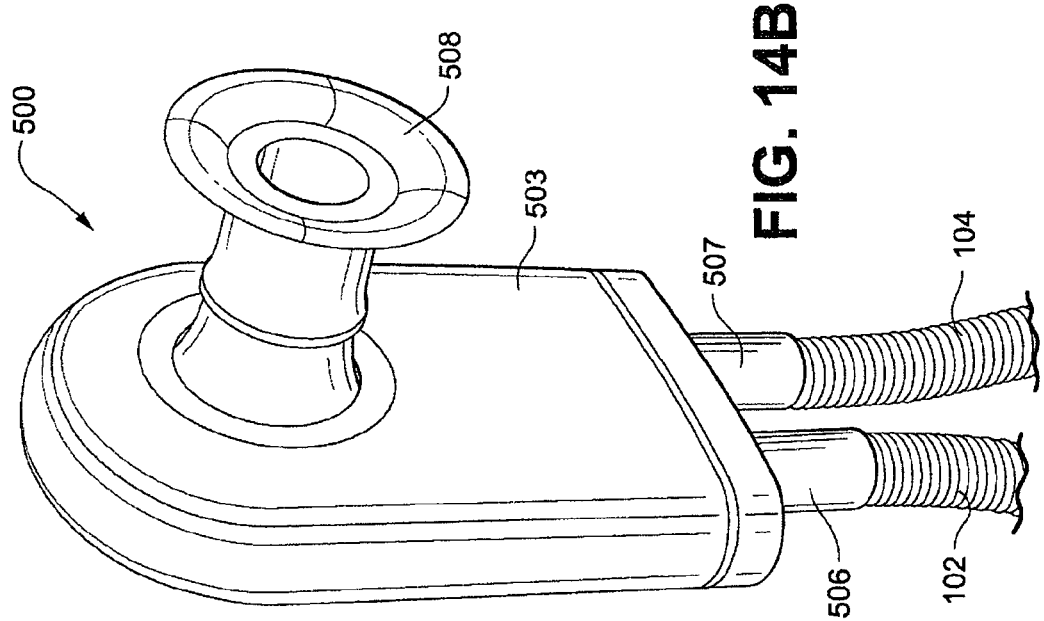
FIG. 14B is a perspective view of the half-biscuit-shaped muffler shown in FIG. 14A showing its suction cup.
Figure 14A:
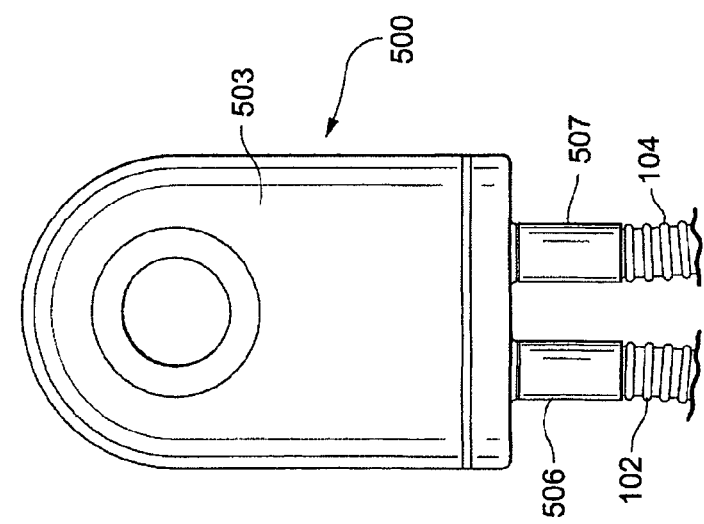
FIG. 14A is a front view of an exemplary half-biscuit-shaped muffler according to an embodiment of the present invention.
Figure 16:
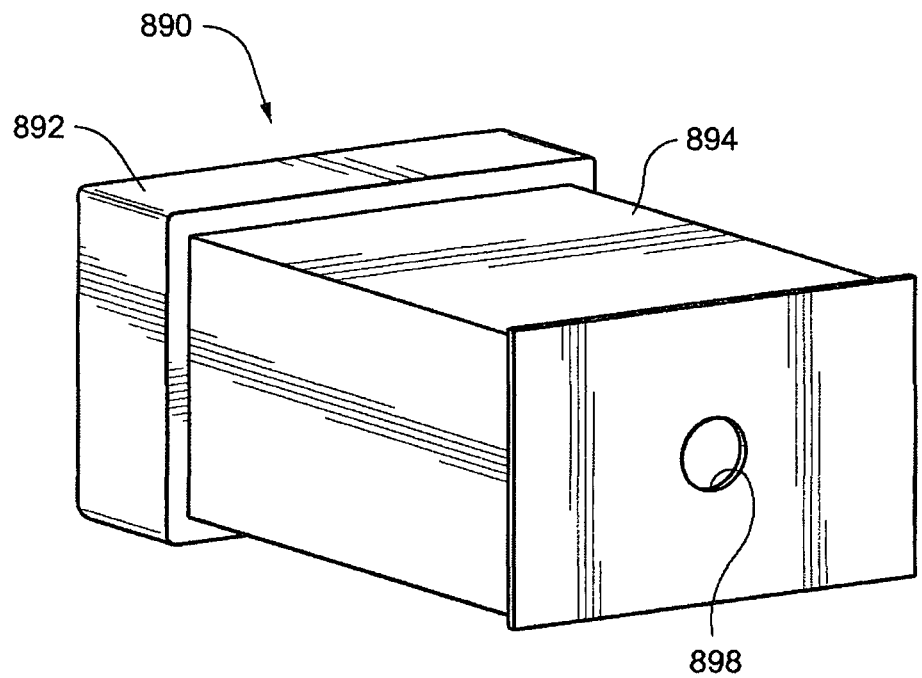
FIGS. 16-30 are various views of an expandable/retractable muffler according to an embodiment of the present invention.

FIGS. 14A and 14B illustrate a half-biscuit shaped muffler (e.g., co-molded with Acrylonitrile butadiene styrene (ABS) and Santoprene™). As illustrated, the muffler 500 includes a main body 503, a first connecting portion 506 adapted to connect to inlet tubing 102, and a second connecting portion 507 adapted to connect to outlet tubing 104. In addition, the muffler 500 includes a suction cup 508 provided to a rear portion thereof. The suction cup is structured to secure the muffler in an operative position, e.g., to a wall, headboard of a bed, nightstand, etc. The suction cup 508 may be structured to swivel with respect to the main body 503, so as to prevent the suction cup 508 from coming under undue tension when the patient moves around.

However, the muffler may include other attachment mechanisms, e.g., hook provided to rear portion. In addition, the muffler may provide tube management options such as the muffler described above. Also, the muffler may be structured to accommodate heated tubing.

2.5 Patient Interface with Muffler

FIGS. 15A and 15B illustrate a muffler 600 incorporated into a patient interface according to an embodiment of the present invention. In this embodiment, the muffler 600 is integrated with the manifold of the patient interface structured to interconnect the patient interface with the air delivery conduit. As shown in FIG. 15A, the patient interface 610 includes an interfacing structure 612 located at the entrance to the patient's airways, a muffler 600 adapted to connect with the air delivery conduit 601, and a pair of tubes 602, 604 to interconnect the interfacing structure 612 and the muffler 600. The inlet tubes 602, 604 are arranged to extend along the sides of the patient's head and near the patient's ears in use.

The muffler 600 includes a main body 603, a first connecting portion 606 (inlet portion) adapted to connect to the air delivery conduit 601, and a pair of second connecting portions 607 (outlet portions) adapted to connect to the tubes 602, 604. The muffler 600 helps to reduce the amount of noise that is transferred or conducted through the system, especially since the tubes 602, 604 extend near the patient's ears in use. In addition, such muffler may also reduce cyclic noise (e.g., noise due to inhalation/exhalation).

2.6 Low Pass/Band Pass Noise Filter

In an embodiment, the mufflers of the previously described embodiments may function, in effect, as a low pass and/or band pass noise filter. For example, the mufflers may be adapted to allow the transmission of low frequency noises (such as snoring) while filtering noises of high frequency (such as noise of the motor of the PAP device). This may allow the control systems of PAP and CPAP to still detect audible snoring of a patient connected to the machine and/or use mask recognition algorithms, e.g., to maintain proper control. Removing or at least ameliorating higher frequency noise generated by the motor of the PAP device may make the general system for the patient less noisy.

In an embodiment, the mufflers generally do not include a tortuous path for the air to follow inside the muffler, which may be different to general muffler design. Additionally, an exemplary configuration may include a straight flow configuration as shown in FIG. 4.

Additionally, an exemplary configuration may include soft walls, intermediate noise baffles, or filters, which may be positioned to filter either high or low frequencies.

In an embodiment, the shape of the muffler may have a shape and configuration resulting in an inherently low impedance relative to the air passing through it. Increases in impedance may significantly reduce low frequency noise which may not be preferred for applications for use with CPAP or PAP equipment. The overall diameter of the main body of the muffler affects the overall impedance, e.g., larger diameters have greater impedance.

2.7 Expandable/Retractable Muffler

Figure 17:
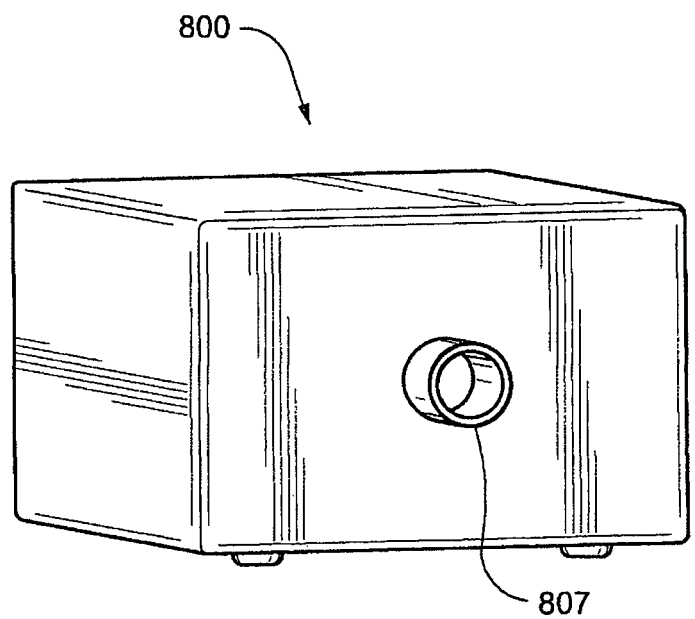
Figure 18:
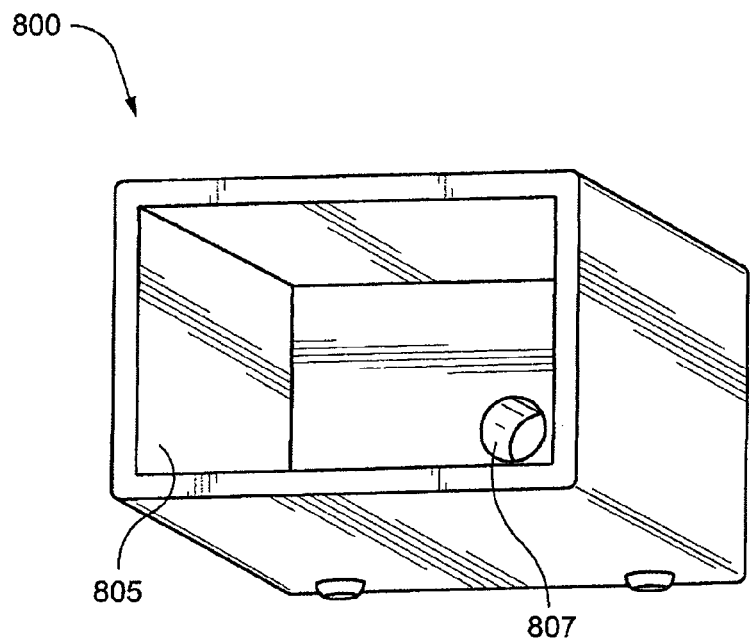
Figure 19:
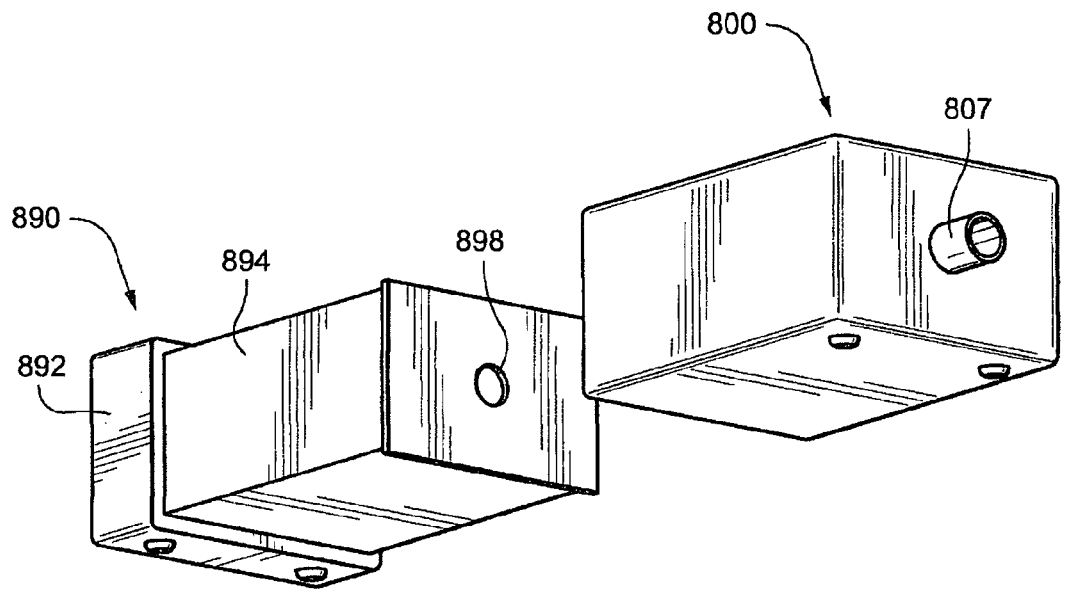
Figure 20:
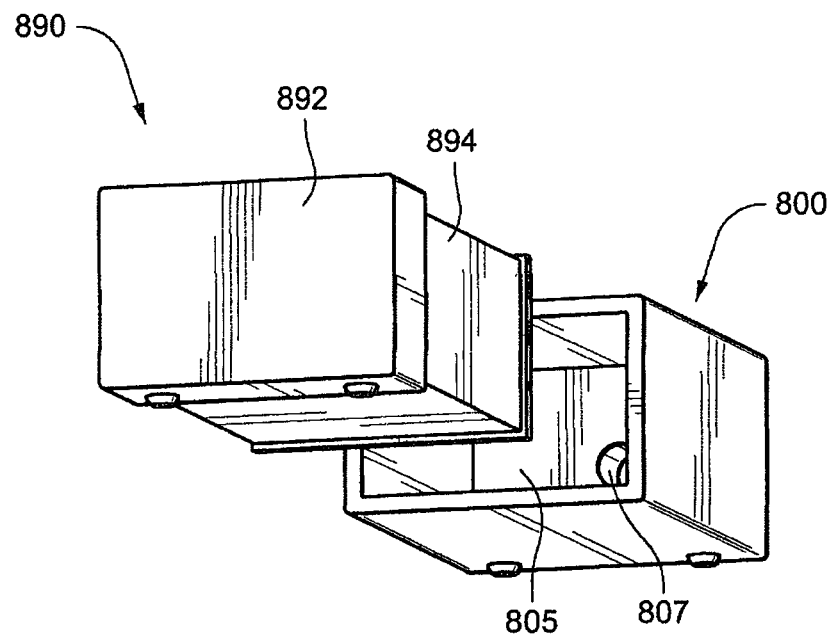
Figure 21:
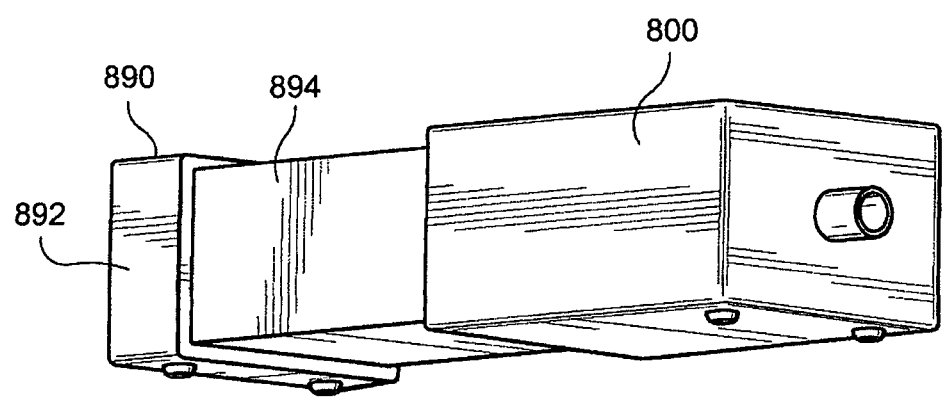
Figure 22:
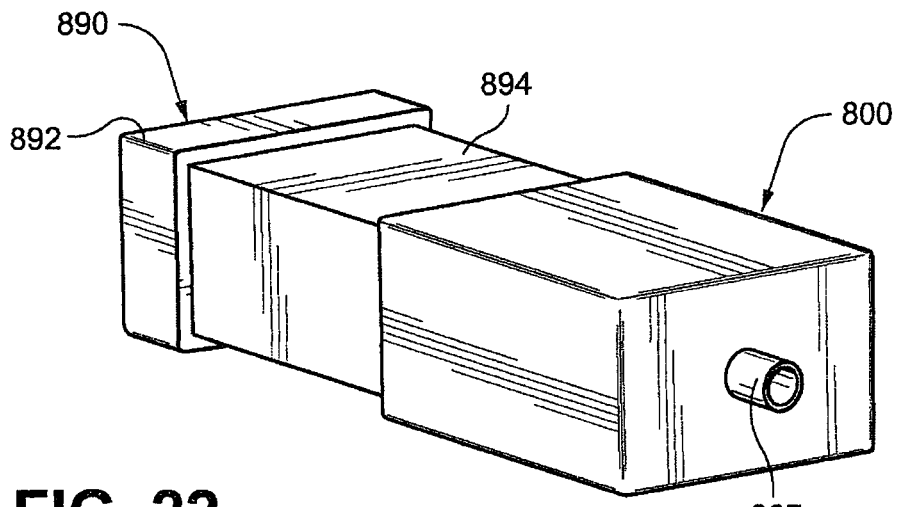

FIGS. 16-30 illustrate an expandable/retractable muffler according to an embodiment of the present invention. In this embodiment, the PAP device 890 includes a casing 892 which provides a protruding portion 894 with a control panel 896 (e.g., see FIG. 30). The muffler 800 is in the form of an outer casing which forms a chamber 805 and is adapted to be mounted to the outer surface of the protruding portion 894 of the PAP device 890 (e.g., see FIGS. 17 and 18), i.e., protruding portion includes smaller circumference than respective chamber of the muffler. As shown in FIGS. 19-30, the PAP device casing nests inside the muffler casing, preferably forming an airtight or near airtight seal. A person skilled in the art may appreciate that there are several methods of securing the muffler to the PAP device in this way.

Figure 23:
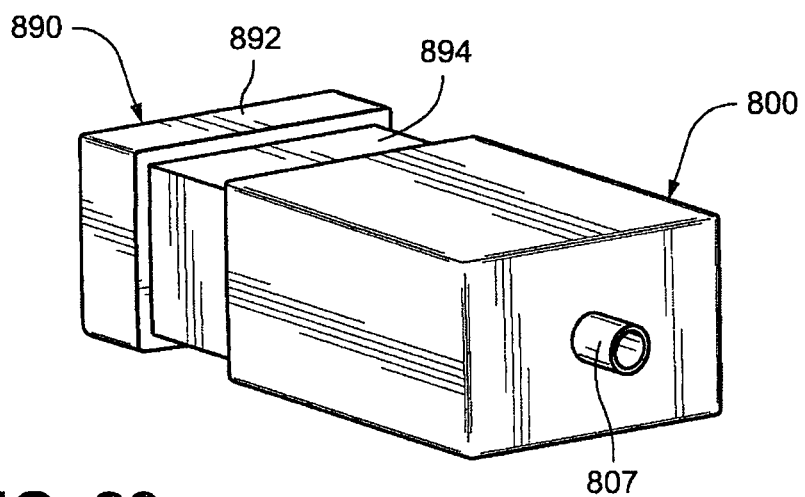
Figure 24:
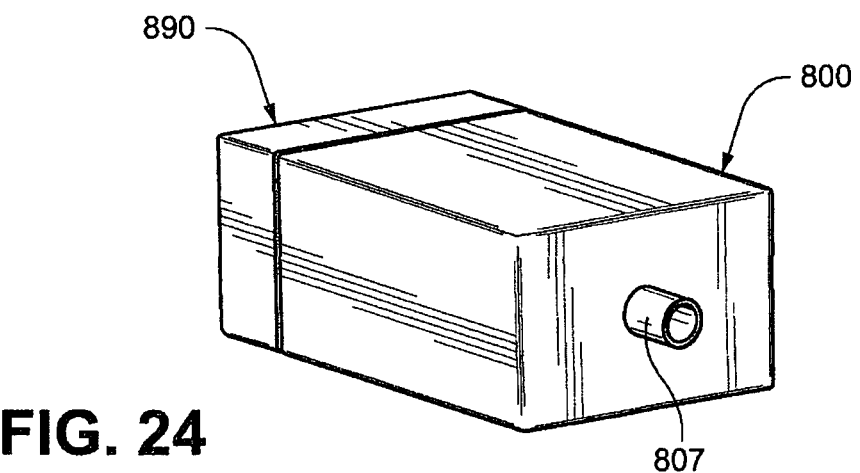
Figure 25:
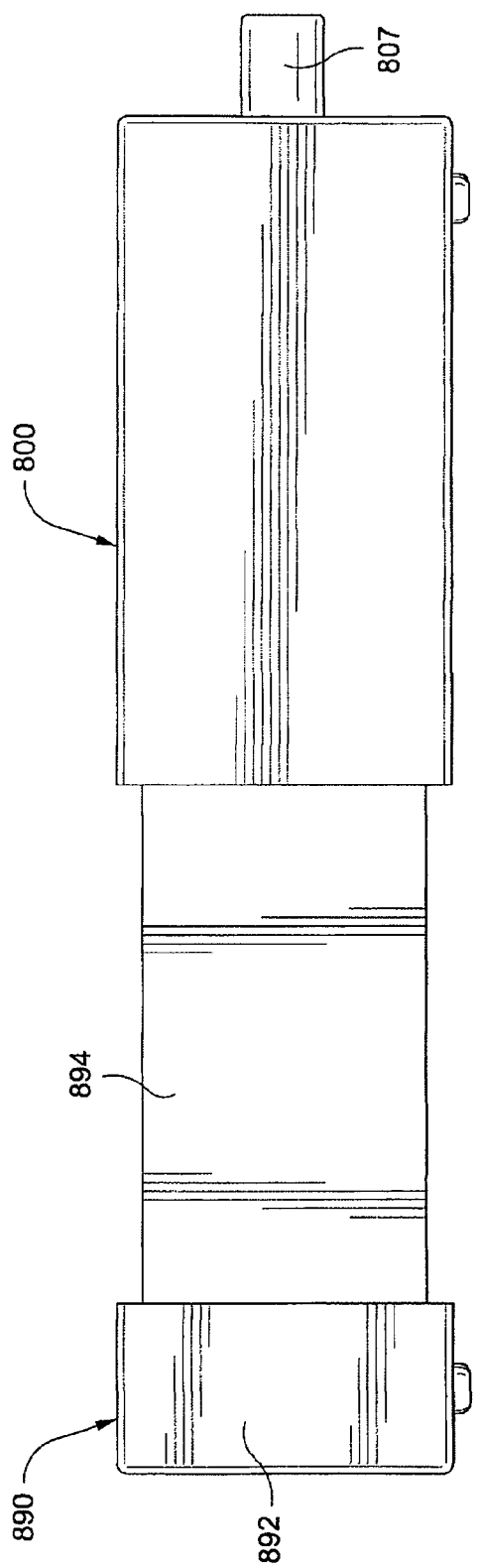
Figure 26:
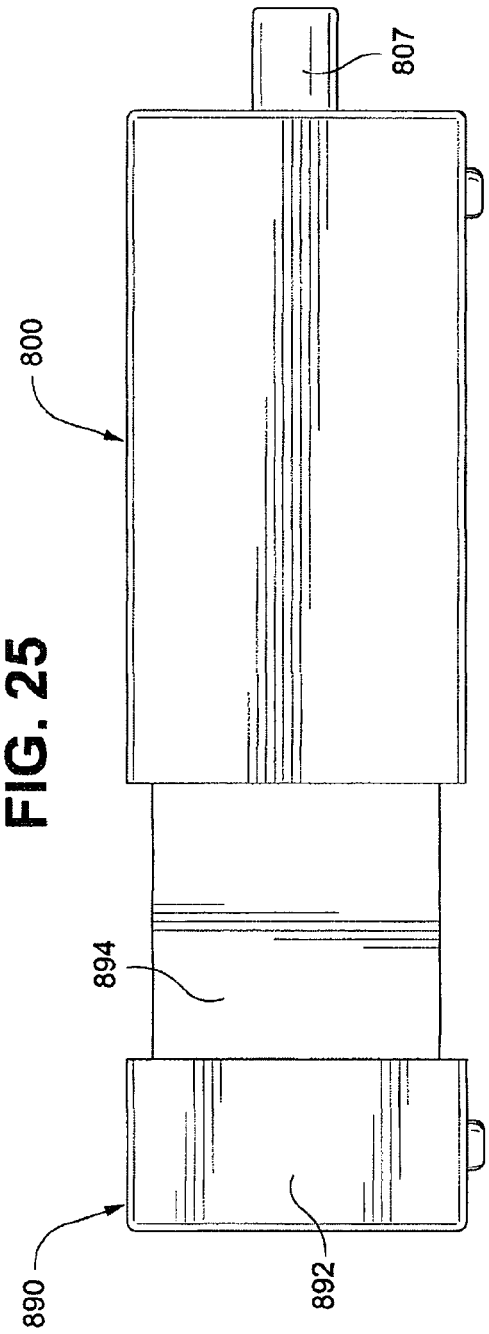
Figure 27:
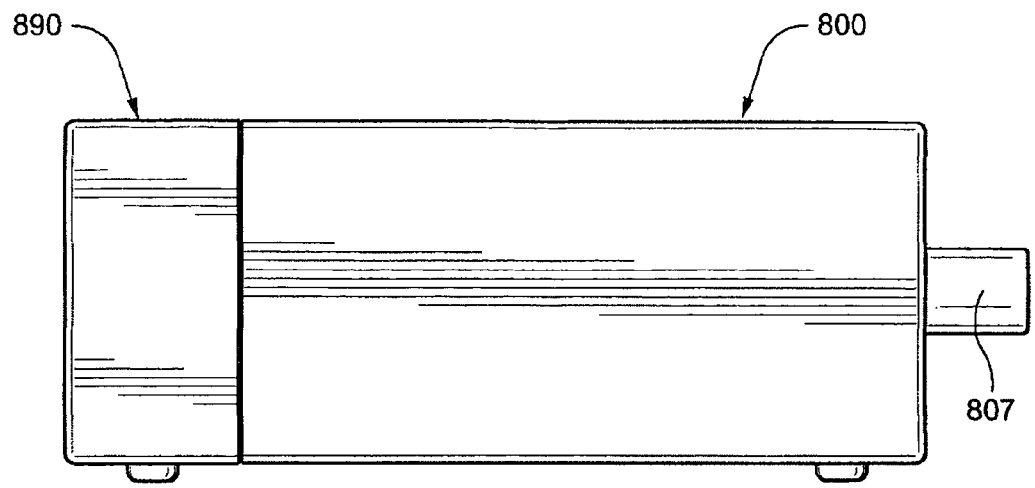
Figure 28:
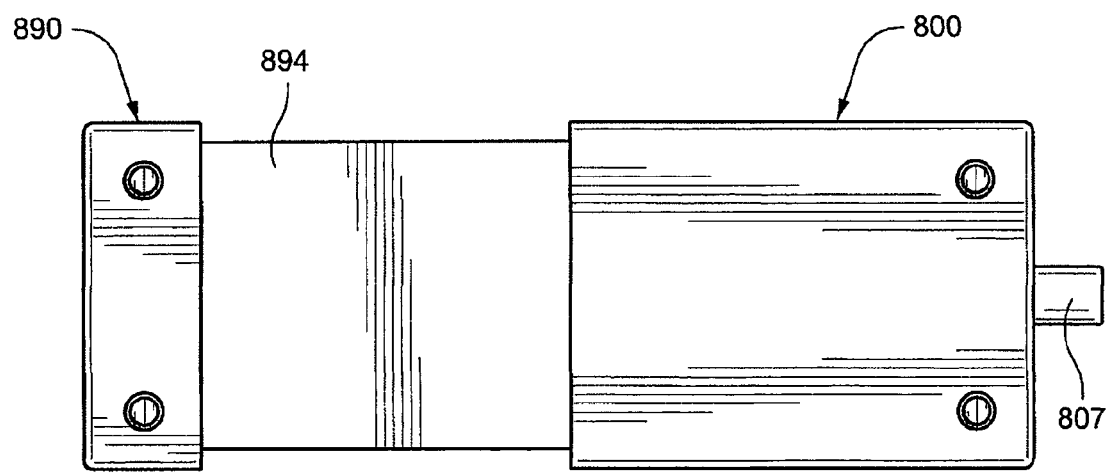
Figure 29:
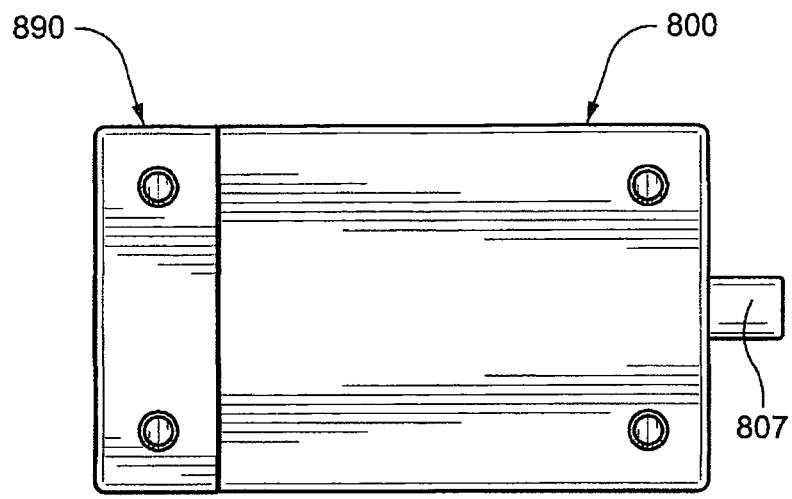

In use, the muffler 800 may slide along the protruding portion 894 and may be selectively fixed in one or more predetermined positions. The predetermined positions may vary the size of the chamber 805 and hence the muffling function. The sliding arrangement of the embodiment allows the PAP device and muffler to be compacted for moving or transporting. FIGS. 22, 25, 28, and 30 show a fully open or expanded position of the muffler, FIGS. 23 and 26 show an intermediate position of the muffler, and FIGS. 24, 27, and 29 show a closed or retracted position of the muffler.

The chamber 805 of the muffler allows for destructive interference to interfere with or cancel out the noise generated by the motor. Air enters the chamber via the outlet 898 of the PAP device 890 and exits the chamber via the outlet 807 of the muffler 800.

Figure 30:
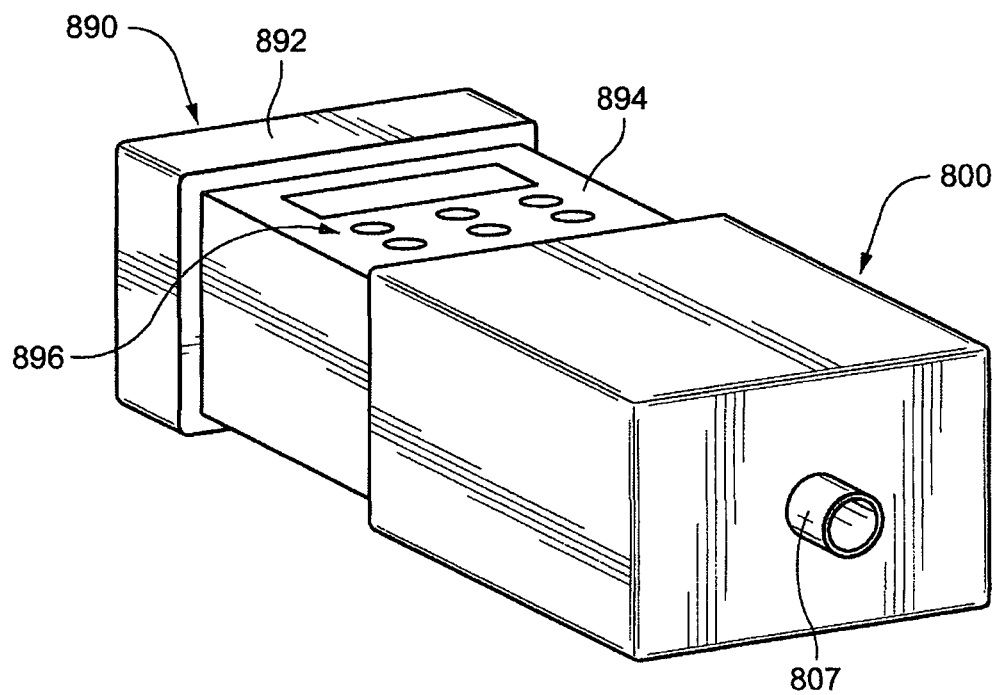

As shown in FIG. 30, the muffler is adapted to cover and protect the control panel 896 of the PAP device when retracted, e.g., muffler hides all the controls and displays within the unit for a sleek, non-medical appearance.

2.8 Further Alternatives and Specifications

In an embodiment, a music playing device may be provided along the air delivery system, such as in the PAP device. Music played at a suitable volume may be transferred along the tubing and delivered, for example, past the patient's ears. Such a system can help mask the noise inherent in the CPAP system, and prevent the patient from having to either wear headphones, having a cord that could lead to problems during sleep, or play music from an external source, which could disturb another sleeper in the room.

In an embodiment, the main body of the muffler may provide a volume or chamber having a volume of about 300-500 mL, which may be suitable for application in a wide range of CPAP systems. In a system producing noise without a muffler, a muffler according to an embodiment of the present invention applied to the system and including a chamber of the above volume may remove 10 dBs or more of noise.

In an embodiment, the muffler may be collapsible for easy transportation when a patient is traveling with a CPAP system. For example, if the muffler was conically shaped, the cylinder could collapse using a series of concentric cylinders (e.g., concertina or telescoping arrangement). In another embodiment, the muffler may be inflatable, e.g., inflates when pressurized to define volume or chamber.

Another option would be to include active noise cancellation technology in the muffler. Active noise cancellation uses a microphone to detect the frequency of present sounds and then uses a speaker to output polarized cancellation sounds designed to counteract the detected sound waves by interference.

Further alternative embodiments may also include additional vent holes (not shown). These vent holes are adapted to be sealed when the device is in use. However, when the muffler is not in use, the vent holes may be opened to allow draining of the internal areas or chamber of the muffler. This may be particularly useful when the system is being used in conjunction with a humidifier (not shown). When a humidifier is connected into the air path, the air increased in humidity often precipitates water along the length of the tubing. The precipitated water may build up and drain into the muffler and the vent holes permit the user to easily drain the system.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A continuous positive airway pressure (CPAP) system for sealed delivery of a flow of breathable gas at a continuously positive pressure to an entrance to a patient's airways, wherein the CPAP system is configured to maintain therapy pressure throughout the patient's respiratory cycle while the patient is sleeping to ameliorate sleep disordered breathing, the CPAP system comprising:
   a positive airway pressure (PAP) device structured to generate a supply of pressurized air;
   a patient interface adapted to engage with the patient's face to provide a seal;
   an air delivery conduit provided between the PAP device and the patient interface to deliver the supply of pressurized air along a gas delivery path from the PAP device to the patient interface; and
   a muffler provided along the gas delivery path downstream of the PAP device,
   wherein the muffler provides an expansion chamber, and the muffler is repeatedly expandable and retractable to be selectively fixed in predetermined positions to vary a size of the chamber.

2. A CPAP system according to claim 1, wherein the muffler includes a main body providing the chamber, a first connecting portion communicated with the PAP device, and a second connecting portion communicated with the patient interface.

3. A CPAP system according to claim 2, wherein the muffler provides an inline arrangement in which the main body and the first and second connecting portions are aligned along an axis of the muffler.

4. A CPAP system according to claim 2, wherein the chamber is visible through a side wall of the muffler.

5. A CPAP system according to claim 1, wherein the muffler includes a filter.

6. A CPAP system according to claim 1, wherein the muffler includes one or more baffles.

7. A CPAP system according to claim 1, wherein the muffler includes a tube connection portion structured to removably attach tubing.

8. A CPAP system according to claim 1, wherein the chamber has a volume of about 300-500 mL.

9. A CPAP system according to claim 1, wherein the patient interface includes a manifold structured to interconnect the patient interface with the air delivery conduit, and the muffler is integrated with the manifold.

10. A CPAP system according to claim 1, wherein each end of the muffler includes a recessed port that extends into the expansion chamber.

11. A CPAP system according to claim 1, wherein the muffler includes a main body and an outer casing that at least partially encloses the main body.

12. A CPAP system according to claim 11, wherein the main body is constructed of plastic and the outer casing is constructed of a soft, elastomeric material.

13. A CPAP system according to claim 1, wherein one or more portions of the muffler are constructed of a transparent material.

14. A CPAP system according to claim 1, wherein the muffler operates at least partially as a low pass and/or band pass noise filter adapted to allow the transmission of relatively lower frequency noise while filtering relatively higher frequency noise.

15. A CPAP system according to claim 1, wherein the muffler includes a main body providing the expansion chamber, a recessed inlet port communicated with the PAP device and extending into the expansion chamber, and a recessed outlet port communicated with the patient interface and extending into the expansion chamber, and wherein the muffler provides an inline arrangement in which the main body, the inlet port, and the outlet port are aligned along an axis of the muffler.

16. A CPAP system according to claim 1, wherein the muffler is in the form of an outer casing which forms the chamber and is adapted to be mounted to a protruding portion of the PAP device.

17. A CPAP system according to claim 16, wherein the muffler is slidably mounted to the protruding portion for movement between expanded and retracted positions.

18. A CPAP system according to claim 1, wherein the muffler is adapted to connect to a relatively short length of tubing from the PAP device and a relatively longer length of tubing to the patient interface.

19. A CPAP system according to claim 1, wherein the chamber is variable in size so that the muffler is tunable to specific muffling requirements.

20. A CPAP system according to claim 1, wherein the muffler with variable chamber size provides a single muffler usable with different PAP devices.

21. A CPAP system according to claim 2, wherein the first and second connecting portions are symmetrical such that the muffler is connectable along the gas delivery path so that the first and second connecting portions are both connectable as either an inlet or an outlet of the muffler.

22. A CPAP system according to claim 21, wherein the first and second connecting portions include a diameter that is the same.

23. A CPAP system according to claim 1, wherein the muffler includes a main body providing the chamber and an outer casing exterior to the chamber and structured to at least partially enclose the main body, the outer casing being constructed of a softer and more flexible material than the main body.

* * * * *